US010254246B2

(12) United States Patent
McNeel et al.

(10) Patent No.: US 10,254,246 B2
(45) Date of Patent: Apr. 9, 2019

(54) METHOD AND APPARATUS FOR MEASURING AND CONTROLLING ELECTROLYTICALLY-ACTIVE SPECIES CONCENTRATION IN AQUEOUS SOLUTIONS

(71) Applicant: Buckman Laboratories International, Inc., Memphis, TN (US)

(72) Inventors: Thomas E. McNeel, Memphis, TN (US); Richard A. Clark, Memphis, TN (US); Richard D. Lusk, Jr., Memphis, TN (US); Chamindu Liyanapatirana, Memphis, TN (US)

(73) Assignee: Buckman Laboratories International, Inc., Memphis, TN (US)

( * ) Notice: Subject to any disclaimer, the term of this patent is extended or adjusted under 35 U.S.C. 154(b) by 1060 days.

(21) Appl. No.: 13/871,073

(22) Filed: Apr. 26, 2013

(65) Prior Publication Data

US 2013/0292267 A1 Nov. 7, 2013

Related U.S. Application Data

(60) Provisional application No. 61/642,193, filed on May 3, 2012.

(51) Int. Cl.
*G01N 27/42* (2006.01)
(52) U.S. Cl.
CPC ................... *G01N 27/423* (2013.01)
(58) Field of Classification Search
CPC .... G01N 27/28; G01N 27/403; G01N 27/416; G01N 27/4161; G01N 27/423
See application file for complete search history.

(56) References Cited

U.S. PATENT DOCUMENTS 2,928,775 A * 3/1960 Leisey ................... G01N 27/44
204/405
4,244,800 A 1/1981 Frazzini et al.
(Continued)

FOREIGN PATENT DOCUMENTS

GB 2237387 A 5/1991
JP 54024698 A * 2/1979

OTHER PUBLICATIONS

J.Lingane, et al., Coulometric Titration of Uranium with Electrogenerated Titanous Ion, Analyticaj Chimica Acta, vol. 13, pp. 465-472 (1955) (Year: 1955).*

(Continued)

*Primary Examiner* — Maris R Kessel
(74) *Attorney, Agent, or Firm* — Kilyk & Bowersox, P.L.L.C.

(57) ABSTRACT

A method is provided for measuring an electrolytically-active species concentration in an aqueous or non-aqueous solution for use in providing control of the concentration of the species in a source solution thereof based on the measurements. In the method, a sample containing an electrolytically-active species is added into a measurement cell that has a working electrode and an auxiliary electrode, and a constant current is applied to the measurement cell while the working and auxiliary electrodes are in contact with the sample with monitoring of voltage difference across the electrodes until a change in the voltage difference is detected. A feedback signal is generated based on a parameter of the change in the voltage difference that is directly proportional to the amount of the electrolytically-active species in the sample, which can be used for process control. An apparatus is also described.

9 Claims, 4 Drawing Sheets (56) References Cited

U.S. PATENT DOCUMENTS 5,470,484 A 11/1995 McNeel
2009/0181107 A1* 7/2009 Buckley .............. C02F 1/46104
424/661

OTHER PUBLICATIONS

W.D. Cooke, et al., Sensitive End-Point Procedure for Coulometric Tritrations, Anal. Chem., vol. 23, No. 11, pp. 1662-1665 (1951) (Year: 1951).*
R T. Chitnis, et al., Determination of Plutonium by Secondary Coulometric Titration with Internally Generated Iron(II), J. of Radioanal. Chem., vol. 49, No. 1, pp. 63-70 (1979) (Year: 1979).*
H. W. Berger, Paint Testing Manual, Constant-current couolometry. Part 10.8, Gardner/Sward, 13th Eidtion. G.G. Sward, Ed. Amer. Soc. Testing Mater. Spec. TEch. Publ., 500, pp. 560-561 (1972) (Year: 1972).*
E. Bishop, et al., Differential Electrolytic Potentiometric Determination of Nanogram Quanities of Halides at Extreme Dilution by Constant Current Coulometry, Anal. Chem., vol. 36, No. 4, pp. 726-730 (1964) (Year: 1964).*
International Search Report and Written Opinion issued in corresponding International Patent Application No. PCT/US2013/038320 dated Jun. 28, 2013 (10 pages).
Kyoo, Dong Jo, "Development of New Automated Flow Titration Systems," Aug. 2004 (135 pages).

* cited by examiner

METHOD AND APPARATUS FOR MEASURING AND CONTROLLING ELECTROLYTICALLY-ACTIVE SPECIES CONCENTRATION IN AQUEOUS SOLUTIONS

This application claims the benefit under 35 U.S.C. § 119(e) of prior U.S. Provisional Patent Application No. 61/642,193, filed May 3, 2012, which is incorporated in its entirety by reference herein.

FIELD OF THE INVENTION

The present invention relates to a method for measuring and controlling an electrolytically-active species concentration in aqueous solutions. The present invention also relates to an apparatus which is useful for such measurements and control.

BACKGROUND OF THE INVENTION

Measurement of quantities of an electrolytically-active species in aqueous solution previously has been done by a variety of analytical techniques. These techniques have had various respective drawbacks.

Controlled potential coulometric analysis is one method in this respect. As explained, for example, in U.S. Pat. No. 4,244,800, controlled potential coulometry is a method of measuring the quantity of a particular electrolytically-active species in a solution by carrying out an electrochemical reaction involving the electrolytically-active species to be measured. The reaction chosen involves the passage of an electric current and knowledge of the oxidation states of the reactants. The amount of current that flows while the reaction proceeds to a determinable fraction of completion provides a measure of the quantity of the substance in solution. The controlled potential coulometric method typically is carried out using a controlled potential coulometer with a three electrode configuration. The device typically is used for controlling the potential of a working electrode to a selected potential with respect to a reference electrode by applying enough voltage and passing enough current between the working electrode and a counter electrode to cause this selected potential to be maintained. The value of the control potential is selected to favor the particular reaction that is desired and thus to discriminate against unwanted reactions. As also explained in the indicated U.S. Pat. No. 4,244,800, several problems generally arise in the making of precise and accurate measurements by conventional controlled potential coulometry. The first is the fact that to permit the reaction to proceed substantially to completion often takes an appreciable amount of time using conventional analysis arrangements. The lengthy analysis time also leads to another problem of increased chance of changes in parameters, such as temperature, during the measurement period that can produce error in the readings. To reduce analysis time, an empirical end-point method may be used, which refers to a technique in which the analysis is terminated at what is believed to be a predetermined fraction of the final value. Methods of coulometry previously used in which the reaction is not carried to completion have possibilities for error that are unacceptable for highly accurate quantitative measurement of substances in solution.

Chemical titration is another analytical technique for determining quantities of an electrolytically-active species in aqueous solution. For example, on-line chemical titration equipment is commercially available, which feasibly could be adapted for use with an existing iodometric method, which involves the following reactions:

Two solutions are required for this iodometric determination (i.e., acidified KI and sodium thiosulfate titrant), and the supplies of these solutions at the analysis location would have to be periodically replenished to continue use of the analysis. Furthermore, the acidified KI solution is subject to oxidation by atmospheric oxygen, so its shelf life is very limited. These requirements can lead to a significant maintenance burden for the operators.

On-line equipment for colorimetric analyses is available from Hach Co. (Loveland, Colo. U.S.A.) and other equipment suppliers. One type of colorimetric test that can be applied by these types of measurement devices involves the known DPD (N,N-Diethyl-Phenylene Diamine) procedure. This method is a nonspecific test that simply detects the presence of any oxidizing agents in the sample. A more specific colorimetric test that is used by these devices involves the reaction of monochloramine with an alkaline solution of a phenol to form a type of Indophenol Blue dye. Again, in these measurement systems, there are several solutions that would have to be replenished from time to time, as well as periodic replacement of pump tubing and other expendable parts. Furthermore, a very large dilution would be necessary for some oxidant chemistries of commercial interest in order to reach the operating range of the measurement devices. This dilution can introduce serious errors in the measurement. Further, it would not be possible to monitor small variations in a total oxidant level, where these dilution errors arise and become problematic. In addition, these colorimetric devices can have a high unit cost. Further, on-line colorimetric equipment can require pumps to keep a portion of fluid flowing through optical cells, which can involve additional moving parts which can be subject to failure.

Polarographic measurements also have been investigated, which use platinum and glassy carbon electrodes. Reproducibility and signal drift have been found to be serious problems, rendering this approach unfeasible. Also, platinum electrodes are oxidized by halogen-containing compounds, such as halogen-containing oxidants, which makes them an undesirable choice for use with those chemistries.

The present investigators have recognized that there is a need for techniques and equipment for measurement of the total quantities of an electrolytically-active species in samples of aqueous solution to provide rapid and accurate analyses of species concentrations in samples of process fluids, which can be used to improve process control and avoid or reduce the indicated drawbacks of other analytical techniques and equipment used therefor.

SUMMARY OF THE PRESENT INVENTION

A feature of the present invention is to provide a method for measuring and/or controlling a total electrolytically-active species concentration in an aqueous solution.

An additional feature of the present invention is to provide a rapid and accurate method for measuring total electrolytically-active species concentration in an aqueous solution for use in providing improved control of the concentration of the species in a source solution thereof.

Another feature of the present invention is to provide a method for measuring and/or controlling electrolytically-active species concentration in an aqueous solution by providing a coulometric measurement procedure wherein the species can be reduced or oxidized electrolytically and the current can be integrated to generate a feedback signal that is directly proportional to the amount of the species in the solution, wherein the feedback signal can be used for controlling a rate of feeding of at least one reactant to a reaction mixture in which the electrolytically-active species is produced.

An additional feature of the present invention is to use the indicated methods for measuring and controlling total oxidant concentration in aqueous solutions.

Another feature of the present invention is to provide a robust, low-maintenance, low-cost apparatus for measuring and controlling the concentration of an electrolytically-active species in an aqueous solution, which can make the indicated measurements of total amount of the species in samples and generate feedback signals for process control based on these measurements.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates, in part, to a method for measuring and/or controlling the concentration of an electrolytically-active species in an aqueous solution, which comprises steps a)-c). In step a), a sample comprising an electrolytically-active species is introduced in a selected amount into a measurement cell, wherein the measurement cell comprises a working electrode and an auxiliary electrode. In step b), a constant current is applied to the measurement cell while the working and auxiliary electrodes are in contact with the sample with monitoring of voltage difference across the working and auxiliary electrodes until a change in the voltage difference is detected. In step c), a feedback signal is generated based on a parameter of the change in the voltage difference. The measured parameter of the change in the voltage difference is directly proportional to the amount of the electrolytically-active species in the selected amount of the sample.

The present invention also relates to a method for measuring and/or controlling the concentration of an electrolytically-active species in an aqueous solution, which comprises steps a)-e). In step a), at least a first reactant and a second reactant are combined to produce a reaction mixture comprising an electrolytically-active reaction product in aqueous solution. In step b), a sample of the reaction mixture is introduced in a selected amount into a measurement cell, wherein the measurement cell comprises a working electrode and an auxiliary electrode. In step c), a constant current is applied to the measurement cell while the working and auxiliary electrodes are in contact with the sample with monitoring of voltage difference across the working and auxiliary electrodes until a change in the voltage difference is detected at the end of a measured duration of time of applying the constant current. In step d), a feedback signal is generated using the measured duration of time of step c), wherein the measured duration of time is directly proportional to amount of the electrolytically-active reaction product in the selected amount of the sample. In step e), the feedback signal of step d) is used to control a rate of feeding of at least one of the first reactant and the second reactant in step a). The series of steps b)-e) can be used once or repeated any number of times.

The present invention also relates to a method for measuring and controlling the concentration of an electrolytically-active species in an aqueous solution treated with the electrolytically-active species, which comprises steps a)-e). In step a), an electrolytically-active product, such as a biocide or other treatment agent, is introduced into (or formed in) an aqueous system (such as an aqueous solution) or other system or area to be treated. The electrolytically-active product can be formed in situ or before introduction in an aqueous solution to provide a treated aqueous solution. The electrolytically-active product can be formed wherein at least a first reactant and a second reactant are combined. In step b), a sample of the treated aqueous solution is introduced (e.g., in a selected amount) into a measurement cell, wherein the measurement cell comprises a working electrode and an auxiliary electrode. In step c), a constant current is applied to the measurement cell while the working electrode and auxiliary electrode are in contact with the sample with monitoring of voltage difference across the working electrode and auxiliary electrode until a change in the voltage difference is detected at the end of a measured duration of time of applying the constant current. In step d), a feedback signal is generated using the measured duration of time of step c), wherein the measured duration of time is directly proportional to amount of the electrolytically-active product in the sample. In optional step e), the feedback signal of step d) can be used to control a rate of feeding of the electrolytically-active product, a component thereof, or precursor thereof in step a). The series of steps b)-e) can be used once or repeated any number of times.

The present invention also relates to an apparatus for measuring and/or controlling the concentration of an electrolytically-active species in an aqueous solution, which comprises a measurement cell and a measurement circuit. The measurement cell comprises a working electrode, an auxiliary electrode, and structure defining a cell volume for receiving a fixed amount of sample comprising an electrolytically-active species in an aqueous solution. The measurement circuit is connected to the working electrode and the auxiliary electrode, wherein the measuring circuit is operable to i) provide a constant current to the measurement cell, ii) monitor and detect a change in voltage difference across the working and auxiliary electrodes, and iii) generate a feedback signal based on a measured parameter of the change in the voltage difference, wherein the measured parameter of the change in the voltage difference is directly proportional to the amount of the electrolytically-active species in the selected amount of the sample.

Instead of an aqueous solution, a non-aqueous solution can be used.

As used herein, a "constant current" refers to a current being applied to a measurement cell for a duration of time with a deviation range of ±5% or less (0-5%) as determined as the percentage difference between the lowest and highest current values relative to the highest current value for the duration of time that the current is applied until the change in voltage difference. For example, a current applied in a range of values of 99 mA as the lowest value to 100 mA as the highest value would have a deviation range of 1% ((100-99/100)*100), and thus would be considered a constant current. A current can be constant current which has a deviation range such as 0-5%, 0-4%, 0-3%, 0-2%, 0-1%, 0-0.5%, 0-0.1%, 0.1%-5%, 0.1%-4%, 0.1-3%, 0.1-2%, 0.1%-1%, 0.25%-5%, 0.25%-4%, 0.25%-3%, 0.25%-2%, 0.25%-1%, 0.5-5%, 0.5%-4%, 0.5%-3%, 0.5%-2%, or any other ranges based on these values, or the deviation range can be below detectable limits. This deviation range will have a direct influence on the accuracy with which the concentration of the electrolytically-active species is determined.

As used herein, an "electrolytically-active species" refers to a species that can undergo an electrochemical reaction in aqueous solution in response to an applied current through the solution.

As used herein, "electrolytically-active" refers to the capability of a species to be oxidized or reduced when electric current is conducted through an aqueous solution containing the species.

As used herein, "species" can refer to compounds in their dry form or at least partially solvated form. For example, a species can be a salt in dry or otherwise non-solvated (e.g., non-dissolved) form, a solvated ionic or nonionic species in aqueous solution, or combinations of these. As indicated, the species may be nonionic, such as monochloramine ($NH_2Cl$).

It is to be understood that both the foregoing general description and the following detailed description are exemplary and explanatory only and are intended to provide a further explanation of the present invention, as claimed.

The accompanying drawings, which are incorporated in and constitute a part of this application, illustrate some of the features of the present invention and together with the description, serve to explain the principles of the present invention.

DETAILED DESCRIPTION OF THE PRESENT INVENTION

The present invention relates in part to a method for rapid and accurate measurement of electrolytically-active species concentration in an aqueous solution for use in providing improved control of the concentration of the species in a source solution thereof. In the method, a sample containing an electrolytically-active species can be added in a selected amount into a measurement cell that has a working electrode and an auxiliary electrode, and a constant current is applied to the measurement cell while the working and auxiliary electrodes are in contact with the sample with monitoring of voltage difference across the electrodes until a detectable change in the voltage difference occurs. A feedback signal is generated based on a parameter of the change in the voltage difference that is directly proportional to the amount of the electrolytically-active species in the selected amount of the sample. The feedback signal can be used for process control. The measured parameter of the change in the voltage difference can be, for example, a measured duration of time of applying the constant current through the sample in the cell until the voltage difference is detected.

An apparatus also is provided which can be used to perform the indicated method. The apparatus has the measurement cell and a measurement circuit that is interoperable therewith. The measurement cell can be configured as a two-electrode cell. For example, the two-electrode cell can have a working electrode, such as a cathode, and an auxiliary or counter electrode, such as an anode, without need of any additional electrodes for providing the cell functions described herein. When a constant current is applied to the measurement cell, the voltage drop across the working and auxiliary electrodes can be relatively small as long as readily-reducible species (or readily-oxidizable as applicable) species is present in the cell. When all of the electrolytically-active species in a sample has been reduced (or oxidized as applicable), the applied voltage must increase to maintain the constant current. The length of time that elapses between the initial application of the constant current until the increase in applied voltage occurs is directly proportional to the amount of oxidant (or reducing agent as applicable) in the cell. Specifically, the measurement circuit can detect the voltage difference change corresponding to a coulometric titration end-point for the sample in the cell, and can generate a feedback signal proportional to a parameter associated with the voltage difference change, such as the duration of time that elapses between initial application of the constant current until the increase in the applied voltage occurs. The measurement circuit is robust and configured to provide an adequate constant level of current to the cell. A differential voltage measurement made across a measurement cell of the indicated apparatus having only the working and auxiliary electrodes as electrodes can be sufficient to detect the point at which an electrolytically-active species, such as an oxidant, has been depleted and the water itself is broken down (forming hydrogen and oxygen) to maintain the constant current. A reference electrode is not required to make these measurements, and thus a three-electrode configuration of the cell is not required in an apparatus of the present invention.

Many oxidant products, the reactants used to make them, or both, can have a very short life span (and/or are not stable) with regard to potency/efficacy. For instance, in water treatment (or other treatments of aqueous solutions) with biocides, for example, it can be important to be able to constantly monitor the oxidant concentration in treated solutions to maintain proper potency thereof. The systems of the present invention can be used, for example, to constantly monitor the total concentration of oxidant in a solution that is being treated or has been treated with an oxidant. The oxidant can be generated in-situ in the treated solution or prepared in advance before addition to the solution. Using the systems of the present invention, analysis results can be obtained in a relatively short period of time based on samples drawn from a source solution of interest, such as a treated water, and used to rapidly generate feedback signals for process control based on the analysis results.

The coulometric measurement system of the present invention can have many advantages, including the capability to rapidly and accurately measure the concentration of an electrolytically-active species in an aqueous solution based on relatively small samples drawn or diverted from a source fluid. The feedback signal generation capabilities of the method of the present invention can be used to improve process control, such as in reaction chemistries related to oxidants in the reaction products, in the reactants, or both. The coulometric measurement method of the present invention further offers several advantages over the indicated alternative techniques for quantitative analysis of electrolytically-active species. For example, the measurement procedure of the present method does not require any additions of analysis chemicals, such as the titrants or color-development reagents required by some existing analytical methods. Routine maintenance and chemical costs associated with the analyses can be significantly reduced or avoided. Also, the multiple levels of serial dilution typically required by colorimetric methods are not necessary in the present invention. In this manner, dilution errors can be eliminated. In addition, an apparatus of the present invention can be assembled with components at lower cost than the unit costs of existing commercially-available on-line titration or colorimetric analytical devices. Further, with fewer moving parts than normally encountered with on-line titration or colorimetric equipment, the coulometric cell used in the present invention can have fewer failure modes, and consequently can be more reliable.

The systems of the present invention can have wide applications. They can be used anywhere that detection and process control are needed or desired with respect to reactants or treatment compounds used in aqueous solutions or non-aqueous solutions. The systems can be used, for example, in industrial water treatment (e.g., cooling water, boiler water, influent/effluent treatment, process water treatment (e.g., pulp, paper), disinfection of potable water, disinfection for food-processing applications (e.g., food sterilizing baths, food washing/rinsing baths, food chiller baths, food heating baths, or other aqueous systems which can be used in food processing), waste water treatment, municipal water treatment, and any other system or process in which bleach, chlorine, bromine, or other oxidizing agents are used or wherein reducing agents are used. The electrolytically-active species that are oxidants, for example, may be used as biocides and/or for other purposes in these various aqueous systems. It will be appreciated that some electrolytically-active compounds can be an oxidizing agent in some reaction chemistries and a reducing agent in other reaction chemistries.

Figure 1:
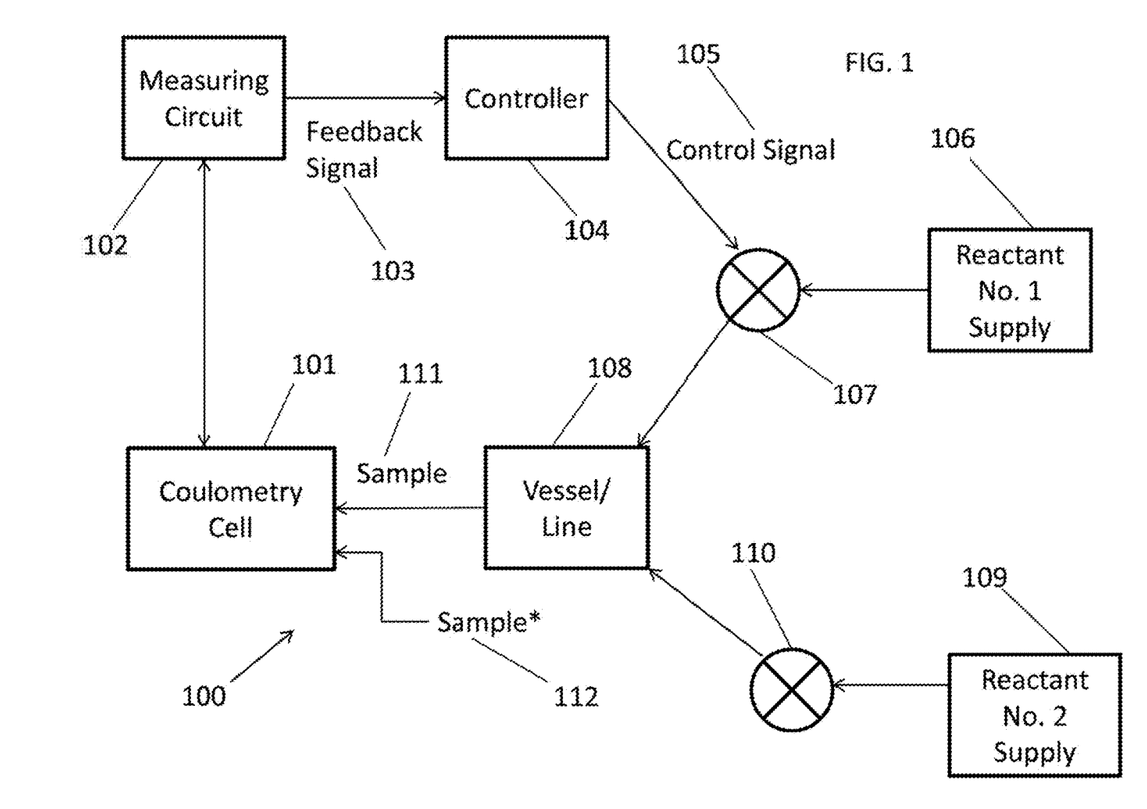
FIG. 1 is a block diagram of a system for measuring and controlling electrolytically-active species concentration in an aqueous solution according to an example of the present application.

Referring to FIG. 1, a system 100 of the present invention is shown which, in this non-limiting illustration, includes a coulometry cell 101 (also referred to herein as the "measurement cell") and a measuring circuit 102 used to detect and measure the total amount of electrolytically-active species in a sample 111 introduced into the coulometry cell 101. Reactant 1 is fed from a supply 106 and Reactant 2 is fed from supply 109 to a vessel or flow line 108 to form a mixture, such as a reaction mixture, from which an electrolytically-active reaction product is produced in this illustration. It will be appreciated that the system 100 can be applied, for example, to treatment of aqueous solutions, such as waters, pulps, aqueous containing streams, and the like, with oxidant chemicals, wherein the reactants used to make the oxidant can be combined directly in the solution for in-situ production of the treatment oxidant or alternatively, the reactants can be combined in advance of the solution to be treated. As another alternative, the reactants can be combined in a vessel/chemical reactor for production of an oxidant chemical product itself. The measuring and control system of the present invention can be applied to these and other applications. Further, for sake of simplifying this illustration, the vessel or line in which the reactants are shown to be combined is also illustrated as the vessel or line from which the sample 111 is drawn for delivery to coulometry cell 101 for analysis. It will be appreciated that the sample can be drawn from a separate vessel or line in fluid communication with the vessel or line that initially received the reactants. Vessel or line 108 can be, for example, a tank, pipe, conduit, reactor, bath, stream, or container, and the like. Additional reactants, not shown in this illustration, can be used depending on the reaction chemistry involved. Sample 111 is a sample of the reaction product that is drawn or diverted from the solution in the vessel or line 108 to the coulometry cell 101 for quantitative analysis. The cell 101 can be designed to hold a fixed volume of sample, so that a coulometric determination of the total amount of species in the sample filled into cell 101 also provides its concentration value (e.g., mass/vol or mol/vol). The measuring circuit 102 can produce a feedback signal 103 that is directly proportional to the amount of the electrolytically-active reaction product in the selected amount of the sample fed into and analyzed in coulometry cell 101. The controller 104 can be programmed, for example, to compare the feedback signal 103 received or acquired from the measurement circuit 102 with a signal that can correspond to a desired level of a reactant, such as Reactant 1 shown in the figure, needed in combination with a known amount of another reactant, such as a known amount of Reactant 2, to produce a desired or selected concentration of reaction product in vessel or line 108. In this respect, controller 104 can send a control signal 105 to a valve or pump 107 or similar flow control means based on the feedback signal 103 to make adjustments in the feed rate of Reactant 1 to vessel or line 108. The feed rate of Reactant 2 to vessel or line 108 can be controlled, for example, using a valve or pump 110. Measurements in cell 101 can be made on well-mixed portions of the reaction solution, for example, after the solution has passed through one or more static mixers and, optionally, a section of tubing that provides a specific delay time (i.e., a reaction coil), before introduced into cell 101. The system can be designed so that the desired reaction has reached completion before the reaction mixture is analyzed in the coulometry cell 101. Sample* 112 shown in FIG. 1 is an option where a sample of one of the reactants, for example, Reactant 1 or Reactant 2, can be fed to the coulometry cell 101 for quantitative analysis. This analysis of the reactant can be done as the only type of sample that is analyzed with the cell 101 or in combination with separate analysis of a sample of the reaction product obtained from the vessel or line 108.

Figure 2:
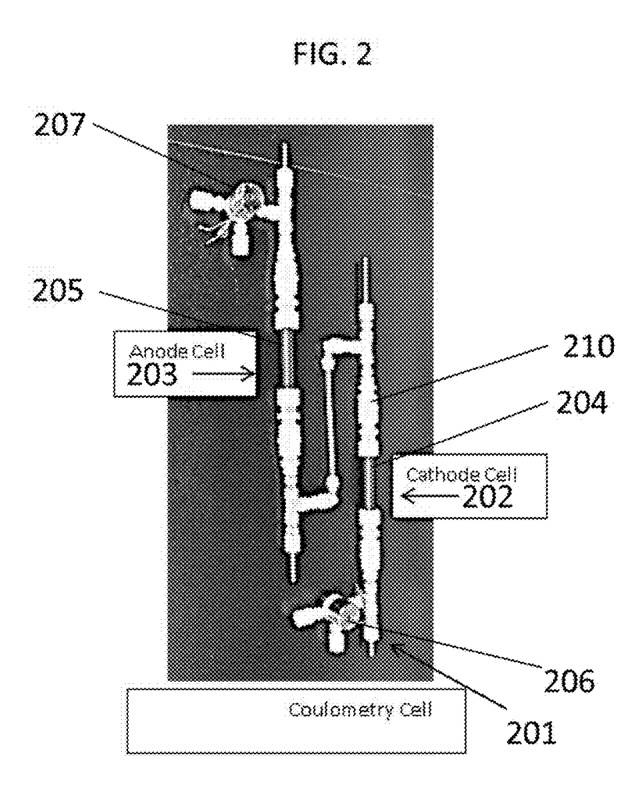
FIG. 2 is a photograph of a typical coulometry cell of the system according to an example of the present application.

Referring to FIG. 2, a typical coulometry cell 201 of the present invention is shown in more detail. The coulometry cell 201 can have a cathode cell 202 near an inlet valve 206 at the lower end of the cell and an anode cell 203 before an outlet valve 207. The lower valve 206 can be a three-way valve, for example, which can permit a sample to be diverted into the cell 201 from a source of fluid (not shown) with the lower valve adjusted to an open flow position or setting relative to the source fluid and with upper valve 207 closed to flow so that hollow interior space defined by the structure of cell 201 can fill up with sample solution. The lower valve 206 then can be closed to trap a fixed volume of the sample inside the cell 201 for quantitative analysis therein. The fixed volume of the sample corresponds to a cell volume 210 defined by the structure of the cell 201. In this manner, a batch-wise, off-line quantitative analysis of samples taken from the system can be performed. The cathode cell 202 can comprise a cathode as working electrode 204 and anode cell 203 can comprise an anode as auxiliary or counter electrode 205. The electrodes 204 and 205 can be materials that are inert, nonoxidizable materials during analysis of the electrolytically-active species in the samples. The electrodes 204 and 205 each can comprise a material that is commonly used as an electrode, such as a hollow graphite tube with a concentric graphite rod. The type of electrode material is not limited to graphite. For example, glassy carbon or other suitable materials can be used as the electrode materials. The tube and rod of the electrodes are connected to positive and negative sides of the applied voltage supply, respectively, which is further discussed herein with respect to the measurement cell in FIG. 3. The design of the electrodes keeps a sample in contact with the electrodes during an analysis. After completion of an analysis on a particular sample, the sample can be drained or flushed out of the system, and then the cell 201 similarly can be refilled with fresh sample for another analysis, and so on. The coulometry cell 201 optionally can be drained by opening the lower valve 206 to allow the sample to flow out of the cell by gravity. The coulometry cell 201 optionally can be flushed between successive analyses performed with the measurement cell, such as by flowing deionized water or other cleaning fluid through the cell, such as by attaching a source of cleaning fluid under pressure at an inlet port of one of the valves 206 and 207, and allowing the cleaning fluid to flow through the cell and emerge from the cell 201 via an open port at the other valve.

Figure 3:
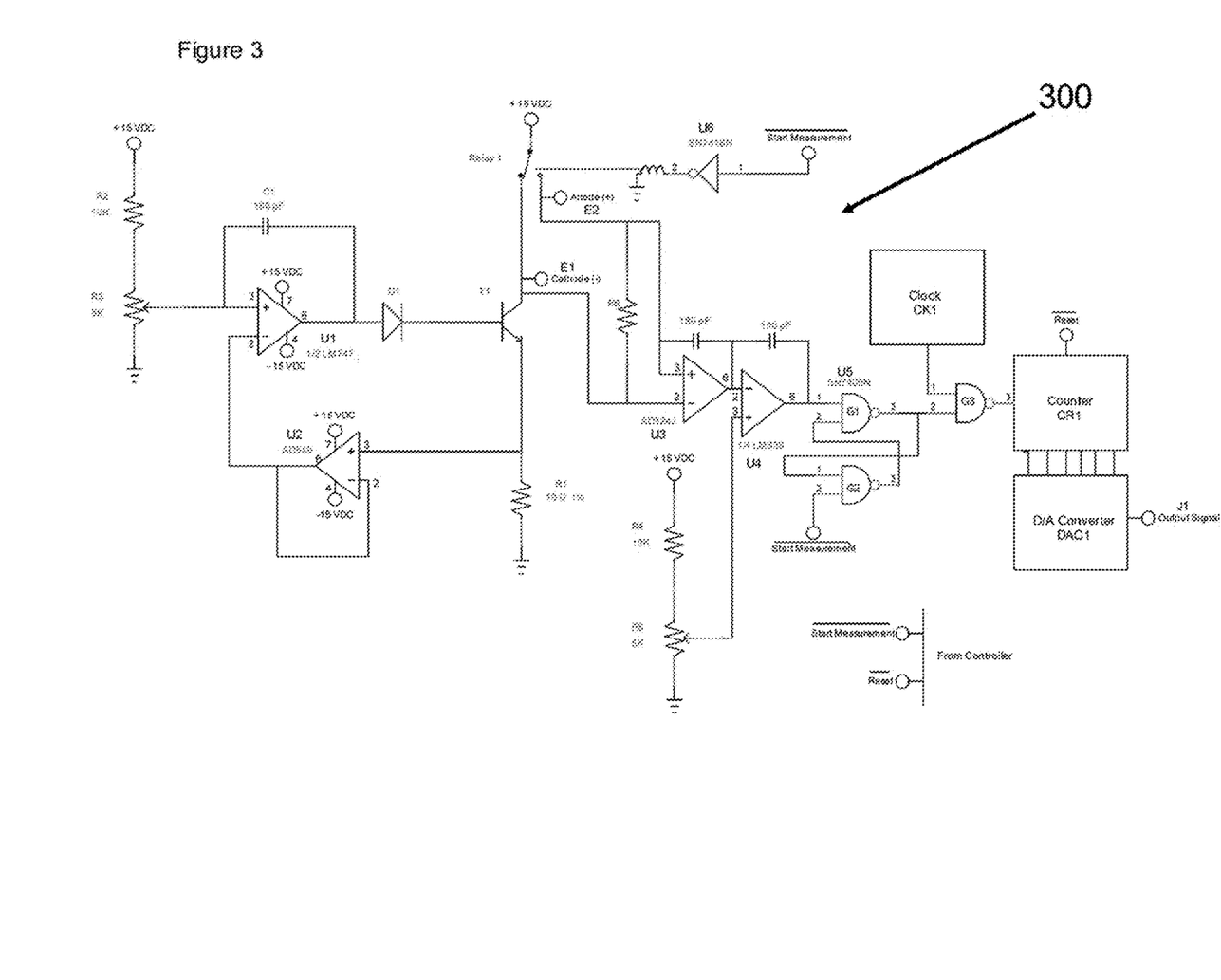
FIG. 3 is a typical circuit diagram of a coulometric measurement circuit of the system according to an example of the present application.

Referring to FIG. 3, an example of a measurement circuit 300 which can be used in systems of the present invention is shown. A two-electrode measurement circuit is provided for producing an output signal at terminal J1, which can be used as a feedback signal for a control system (e.g., such as shown in FIG. 1). An NPN transistor T1 can control the current through the cell and the 10Ω resistor R1 in series with it. The transistor T1 and resistor R1 can force from about 10 mA to about 1 ampere of constant current through the electrodes E1 and E2 (i.e., the measurement cell cathode and anode, respectively). The transistor T1, in turn, can be controlled so that a constant voltage is maintained across the resistor R1. This voltage can be equal to the voltage applied to the noninverting input of the operational amplifier U1, such as ½ of a dual operational amplifier LM747 component manufactured by Texas Instruments Incorporated. Relay 1 (which is controlled by the TTL driver U6) applies the constant current to the electrodes at the beginning of the measurement period and disconnects the cell from the constant current source at the end of the measurement period. The control signal for the relay and driver is provided by the controller 104 in FIG. 1. TTL driver U6 can comprise a SN7416N component manufactured by Texas Instruments Incorporated. Capacitor C1 can be used to prevent oscillation of operational amplifier U1. Resistors R2 and R3 can form a voltage divider which can be used to select the input voltage at amplifier U1. A diode can be placed in the circuit between operational amplifier U1 and Transistor T1. U2 can be a monolithic low power FET-input operational amplifier with a maximum input bias current, which can be an AD549 component manufactured by Analog Devices (Norwood, Mass., U.S.A.). Operational amplifier U3 can be a precision instrumentation amplifier, such as an AD524J component manufactured by Analog Devices. U4 can be ¼ of a quad differential comparator, such as a LM339 component manufactured by Texas Instruments Incorporated. Resistors R4 and R5 can form a voltage divider which can be used to select the input voltage at differential comparator U4. The amplifiers U1, U2, U3, and U4 are shown in FIG. 3 with numbered pins thereof. A 7400 series transistor-transistor logic (TTL) integrated circuit (U5) included in the circuit 300 can include the three NAND gates G1, G2, and G3, each of which can perform a logic NAND function related to the measurement of the duration of time of the application of the constant current. TTL circuit U5 can comprise an SN7400N component manufactured by Texas Instruments Incorporated. Each of NAND gates G1, G2, and G3 can use two pins for input and one pin for its output. A TTL digital clock can be provided by integration of digital clock CK1, NAND gates G1, G2, and G3, and counter CR1. For 7400 series TTL chips, logical "0" can be low voltage and logical "1" can be high voltage. As indicated, when all of the electrolytically-active species in a sample has been reduced (or oxidized as applicable) in the measurement cell, the applied voltage must increase to maintain the constant current, and the length of time that elapses between the initial application of the constant current until the increase in applied voltage occurs is directly proportional to the amount of oxidant in the cell. The duration of time that elapses from initial application of constant current using the measurement circuit until the change in voltage occurs can be timed by the measurement circuit having the illustrated configuration of components. The digital information measured on the measured duration of time of the application of the constant current until the increase in applied voltage can be converted into an analog signal by a digital to analog converter DAC1, which can be outputted at terminal J1 of the circuit. As illustrated, the two-electrode based measurement circuit of FIG. 3 provides a circuit that produces an effective feedback signal at terminal J1 that can be used in a process control system.

The measurement circuit, such as illustrated in FIG. 3, essentially comprises an integrator module which integrates the constant current passing between the working and counter electrodes, wherein the integrated current is a function of its duration of application at a constant value until the increase in applied voltage in the measurement cell is detected, which indicates the end-point of the electrolysis of the species. The integrated current is directly proportional to the total amount of electrolytically-active species electrolyzed in the measurement cell. As the measurement cell volume can be fixed to a constant value, the molar concentration of the species in the sample also can be calculated based on the quantified amount of species and the fixed known amount of sample that was analyzed. The end-point of the measurement system can be identified, for example, in the following manner. The cell can be filled with a blank solution (i.e., a solution in which the oxidant or other electrolytically-active species has been depleted) and the voltage necessary to maintain the constant current is measured. This voltage then can become the endpoint of the coulometric measurement performed on a fresh sample.

An electrolytically-reducible species that can be analyzed by the system of the present invention is not necessarily limited. The electrolytically-reducible species can be, for example, halo-containing oxidant, a peroxide, or a peroxide source. The halo-containing oxidants can be, for example, a haloamine such as monochloramine ($NH_2Cl$), dichloramine ($NHCl_2$), trichloramine ($NCl_3$), monobromamine ($NH_2Br$), dibromamine ($NHBr_2$), tribromamine ($NBr_3$), monoiodamine ($NH_2I$), diiodamine ($NHI_2$), triiodamine ($NI_3$), monofluoramine ($NH_2F$), difluoramine ($NHF_2$), trifluoramine ($NF_3$), or any combinations thereof; an N-halamine sulfonamide such as chloramine T (sodium-N-chloro-p-toluenesulfonamide), dichloramine-T (N,N-dichloro-p-toluenesulfonamide), or any combinations thereof; an alkali hypohalite such as sodium hypochlorite (NaOCl), potassium hypochlorite (KOCl), lithium hypochlorite (LiOCl), sodium hypobromite (NaOBr), potassium hypobromite (KOBr), lithium hypobromite (LiOBr), sodium hypoiodite (NaOI), potassium hypoiodite (KOI), lithium hypoiodite (LiOI), sodium hypofluorite (NaOF), potassium hypofluorite (KOF), lithium hypofluorite (LiOF), or any combinations thereof; an alkaline earth hypohalite such as calcium hypochlorite ($Ca(ClO)_2$), calcium hypobromite ($Ca(BrO)_2$), calcium hypoiodite ($Ca(IO)_2$), calcium hypofluorite ($Ca(FO)_2$), magnesium hypochlorite ($Mg(ClO)_2$), magnesium hypobromite ($Mg(BrO)_2$), magnesium hypoiodite ($Mg(IO)_2$), magnesium hypofluorite ($Mg(FO)_2$), or any combinations thereof; a hypohalous acid such as hypochlorous acid (HOCl), hypobromous acid (HOBr), hypoiodous acid (HOI), hypofluorous acid (HOF), or any combinations thereof; chlorine dioxide ($ClO_2$); a diatomic halogen such as chlorine ($Cl_2$), bromine ($Br_2$), iodine ($I_2$), fluorine ($F_2$), or any combinations thereof. The peroxide and peroxide sources, which jointly can be referred to herein as a peroxy compound, can be, for example, hydrogen peroxide, peroxide salt, perborate, percarbonate, persulfate, peroxyurea compound, persilic acid, percarboxylic acid, peracetic acid, or hydrogen peroxide adduct of urea, pyrophosphate, phosphate, citrate, sodium sulfate, or sodium silicate, or any combinations thereof. Specific examples of peroxy compounds include, but are not limited to, alkali peroxide, alkaline earth peroxide, alkali perborate salt, alkaline earth perborate salt, alkali percarbonate salt, alkaline earth percarbonate salt, alkali persulfate salt, alkaline earth persulfate, peroxyurea compound, persilic acid, percarboxylic acid salt, peracetic acid salt, hydrogen peroxide adduct of urea, pyrophosphate, phosphate, citrate, sulfate, or sodium silicate, or any combinations thereof. Additional examples include without limitation percarbonates like sodium percarbonate, perborates like sodium perborate, peroxides like sodium, magnesium or calcium peroxide, hydrogen peroxide adducts of urea such as urea hydrogen peroxide (carbamide peroxide), and hydrogen peroxide adducts of pyrophosphates and phosphates like sodium phosphate perhydrate.

As non-limiting illustrations, the systems of the present invention can be used to generate a signal that is directly proportional to an assay of bleach (sodium hypochlorite) that can be used (a) as a source of chlorine in industrial processes, or (b) for the on-site generation of other oxidizing biocides, such as sodium hypobromite or monochloramine. The system can also be used to assay these oxidizing biocides as they are generated. In a specific non-limiting example of an application, the system can be used to provide an assay of the monochloramine solution produced by a system that combines bleach with an ammonia solution. This reaction can proceed by the following general equation:

$$NaOCl + NH_3 \rightarrow NH_2Cl + NaOH.$$

The feedback signal for this reaction can monitored by an intelligent digital process controller, which can adjust the bleach feed rate so that the level of monochloramine in the output of the system can be maximized. A coulometric measurement procedure can be used, for example, in which the reaction product ($NH_2Cl$), which is an oxidant, is reduced electrolytically in the measurement system of the present invention, and the cathodic current is integrated to generate a value that is directly proportional to the amount of monochloramine in the solution. If the electrolysis is carried out using a constant current of C amperes, then:

$$NH_2Cl + H^+ + 2e^- \rightarrow NH_3 + Cl^-$$

and the amount of chloramine in an analyzed sample can be calculated by the following equation:

$$gm\ NH_2Cl = \frac{Time\ (seconds)}{} \times \frac{C\ Coulombs}{Second} \times$$

$$\frac{1\ mole\ e^-}{96,500\ Coulombs} \times \frac{1\ Mole\ NH_2Cl}{2\ mole\ e^-} \times \frac{51.5\ gm\ NH_2Cl}{1\ Mole\ NH_2Cl}$$

wherein C=constant cathodic current in amperes. As indicated, as the analysis is performed on a fixed and known volume of sample, then a determination of the mass amount of monochloramine in the sample also permits the concentration of the monochloramine in the sample to be calculated.

Figure 4:
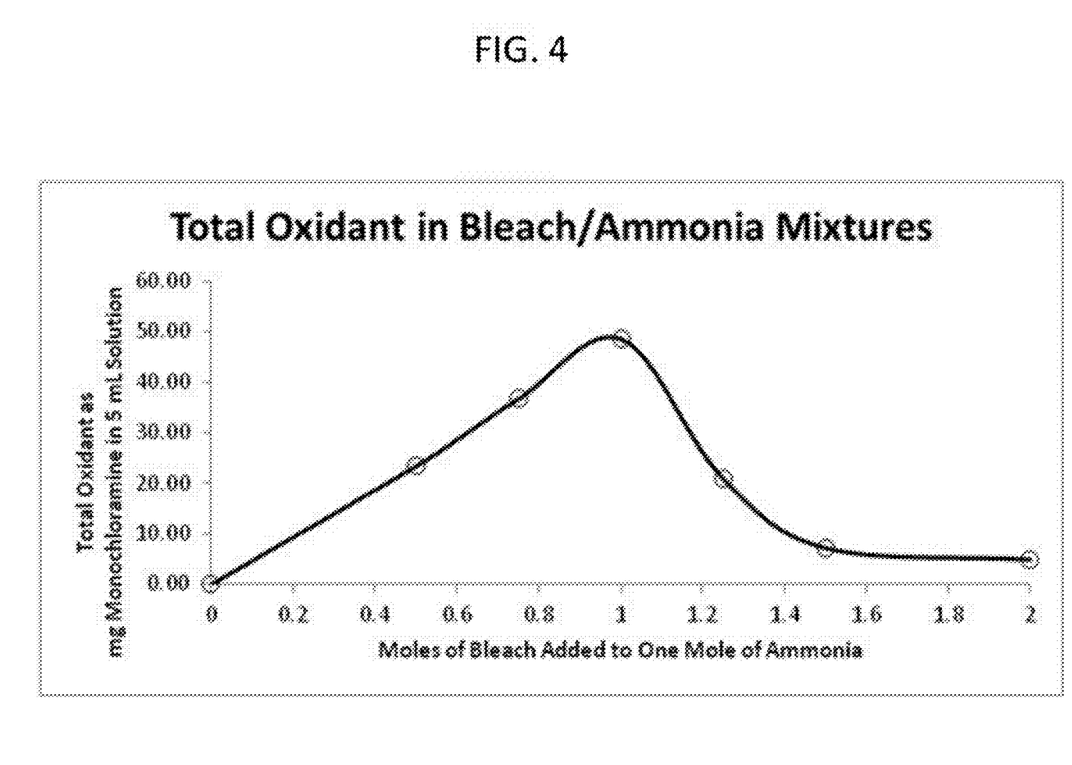
FIG. 4 is a plot showing concentration of chloramine reaction product as a function of moles sodium hypochlorite (bleach) added per mole ammonia in a reaction mixture according to an example of the present application.

The total oxidant concentration of monochloramine product in the reaction mixtures can be very dependent upon the molar ratio of bleach and ammonia used to prepare the mixture. Referring to FIG. 4, several mixtures of bleach and ammonia at different blending ratios thereof were prepared and the reaction products (i.e., monochloramine) produced by the mixtures were analyzed using an iodometric titration procedure and plotted. The results showed that a measurement of total oxidant content, e.g., total monochloramine, can be used to optimize the yield of monochloramine. As shown by FIG. 4, the concentration of total oxidant (monochloramine) in the reaction product made from the reaction of bleach and ammonia can be very sensitive to the molar blend ratio of the reactants with regards to achieving optimal strength. As shown by the data curve in FIG. 4 of this illustration, the concentration of reaction product oxidant (monochloramine) has a maximal value near equimolar blends of the reactants, wherein the potency drops off significantly and rapidly if the relative amount of bleach is too high or low relative to the amount of ammonia used in the reaction. The system of the present invention can provide improved process control to keep the reactant blend ratio at or near the ideal blending ratio, such as shown in FIG. 4, for providing oxidant product in high concentrations. For example, if the ammonia feed rate is fixed, the bleach feed rate can be adjusted up or down until the total oxidant level in the reaction product solution is maximized. The adjustment of the bleach reactant can be based on a feedback signal generated by the indicated measurement cell from an analysis of a sample of the reaction product solution in the indicated coulometry cell. As another example, if the bleach feed rate is fixed, the ammonia feed rate can be adjusted up or down until the total oxidant level in the reaction product solution is maximized based on use of a correlation provided in a similar way with the amount of ammonia used as the reactant variable. The adjustment of the ammonia reactant also can be based on a feedback signal generated by the indicated measurement cell from an analysis of a sample of the reaction product solution in the indicated coulometry cell.

Likewise, a solution of sodium hypochlorite (bleach) can be directly analyzed in a similar manner, wherein:

$$NaOCl + 2H^+ + 2e^- \rightarrow NaCl + H_2O$$

and the amount of bleach in an analyzed sample can be calculated by the following equation:

$$gm\ NaOCl = \frac{Time\ (Seconds)}{} \times \frac{C\ Coulombs}{Second} \times$$

$$\frac{1\ mole\ e^-}{96,500\ Coulombs} \times \frac{1\ Mole\ NaOCl}{2\ mole\ e^-} \times \frac{74.5\ gm\ NaOCl}{1\ Mole\ NaOCl}$$

wherein C=constant cathodic current in amperes.

The cell currents and analysis times can be determined by the volume of solution in the cell as well as the concentration of oxidant in the solution. There can be several practical considerations in the design of the equipment. The applied current used in methods of the present invention can be, for example, in the range of from about 10 mA to about 1 ampere range, or from about 25 mA to about 750 mA, or from about 50 mA to about 500 mA, or from about 100 mA to about 250 mA, or other ranges. High current levels can generate heat in the cell contents, even to levels high enough to damage the cell. The smaller the volume of solution analyzed, the lower the current required for the analysis. However, some solutions for analysis may contain suspended solids, which could clog very small diameter tubing or very thin flow cells if used in the measurement cell or related flow lines. Hence, there are tradeoffs that can be taken into account in the design of a practical device. An example of a sample analysis system design for the indicated reaction system for producing monochloramine with bleach and ammonia reactants is a design which has a test duration of about 100 seconds for a 1% solution of monochloramine. If the cell volume is 6 mL (which can be, for example, approximately 15 cm of ⅜" ID tubing with a ¼ coaxial graphite electrode), a cell current of 100 mA can require about 37 minutes to electrolyze all of the monochloramine in the cell, while a cell current of one ampere can only take about 3.7 minutes. A smaller cell volume thus can reduce analysis times and be more convenient.

The present invention thus relates in part to a robust, low-maintenance, low-cost apparatus for the determination of total electrolytically-active species levels in aqueous solutions and to use an output signal from this apparatus to control the feed of water treatment chemicals to industrial, municipal, and commercial water systems, or other systems.

The present invention includes the following aspects/embodiments/features in any order and/or in any combination:

1. The present invention relates to a method for measuring and controlling the concentration of an electrolytically-active species in an aqueous or non-aqueous solution, comprising:
a) introducing a sample comprising an electrolytically-active species (e.g., in a selected amount) into a measurement cell, wherein the measurement cell comprises a working electrode and an auxiliary electrode;
b) applying a constant current to the measurement cell while the working electrode and auxiliary electrode are in contact with the sample with monitoring of voltage difference across the working electrode and auxiliary electrode until a change in the voltage difference is detected; and
c) generating a feedback signal based on a measured parameter of the change in the voltage difference, wherein the measured parameter of the change in the voltage difference is directly proportional to the amount of the electrolytically-active species in the sample.

2. The method of any preceding or following embodiment/feature/aspect, further comprising reacting at least one reactant before step a) to produce a reaction mixture from which the sample is derived.

3. The method of any preceding or following embodiment/feature/aspect, wherein the reaction mixture comprising an electrolytically-active reaction product in aqueous or non-aqueous solution.

4. The method of any preceding or following embodiment/feature/aspect, wherein the measured parameter of the change in the voltage difference is a measured duration of time of applying the constant current in step b) until the voltage difference is detected.

5. The method of any preceding or following embodiment/feature/aspect, wherein the generating of the feedback signal comprises generating a feedback signal using the measured duration of time, wherein the measured duration of time is directly proportional to an amount of the electrolytically-active reaction product in the sample.

6. The method of any preceding or following embodiment/feature/aspect, further comprising using the feedback signal to control a rate of feeding of at least one reactant to a process unit wherein the reacting occurs.

7. The method of any preceding or following embodiment/feature/aspect, wherein the generation of the feedback signal comprises generating a feedback signal using the measured duration of time, wherein the measured duration of time is directly proportional to an amount of a reactant in the sample.

8. The method of any preceding or following embodiment/feature/aspect, wherein the electrolytically-active species is an oxidizing agent, and the method further comprises combining the oxidizing agent and a second reactant to produce a reaction mixture comprising at least one reaction product in aqueous solution or non-aqueous solution.

9. The present invention relates to a method for measuring and controlling the concentration of an electrolytically-active species in an aqueous solution or non-aqueous solution, comprising:
a) combining at least a first reactant and a second reactant to produce a reaction mixture comprising an electrolytically-active reaction product in solution;
b) introducing a sample of the reaction mixture (e.g., in a selected amount) into a measurement cell, wherein the measurement cell comprises a working electrode and an auxiliary electrode;
c) applying a constant current to the measurement cell while the working electrode and auxiliary electrode are in contact with the sample with monitoring of voltage difference across the working electrode and auxiliary electrode until detecting of a change in the voltage difference at a measured duration of time of applying the constant current;
d) generating a feedback signal using the measured duration of time of step c), wherein the measured duration of time is directly proportional to an amount of the electrolytically-active reaction product in the sample; and
e) optionally, using the feedback signal of step d) to control a rate of feeding of the first reactant and/or the second reactant in step a).

10. The method of any preceding or following embodiment/feature/aspect, wherein the electrolytically-active reaction product is an oxidant.

11. The method of any preceding or following embodiment/feature/aspect, wherein the electrolytically-active reaction product is a halo-containing oxidant, a peroxide, or a peroxide source.

12. The method of any preceding or following embodiment/feature/aspect, wherein the first reactant is an oxidizing agent in solution.

13. The method of any preceding or following embodiment/feature/aspect, wherein the first reactant is an alkali metal hypochlorite, the second reactant is ammonia, and the electrolytically-active reaction product is chloramine.

14. The method of any preceding or following embodiment/feature/aspect, wherein the constant current has a value in the range of from about 10 milliampere (mA) to about 1 ampere (A).

15. The method of any preceding or following embodiment/feature/aspect, wherein the working electrode and the auxiliary electrode independently comprise graphite, glassy carbon, or any combinations thereof.

16. The method of any preceding or following embodiment/feature/aspect, wherein the selected amount of the sample is from about 1 mL to about 10 mL, wherein the measurement cell has a fixed cell volume which defines the selected amount of sample.

17. The method of any preceding or following embodiment/feature/aspect, further comprising:
i) introducing a second sample composed of the first reactant into the measurement cell;
ii) applying a second constant current to the measurement cell while the working and auxiliary electrodes are in contact with the second sample with monitoring of voltage difference across the working and auxiliary electrodes until detecting of a change in the voltage difference at a measured duration of time of applying the second constant current;
iii) generating a feedback signal using the measured duration of time of step ii), wherein the measured duration of time is directly proportional to amount of the oxidizing agent in the second sample; and
iv) using the feedback signal of step iii) to control a rate of feeding of the first reactant in step a).

18. The present invention relates to a method for measuring and/or controlling the concentration of an electrolytically-active species in an aqueous or non-aqueous solution treated (e.g., to be treated, and/or currently being treated, and/or after being treated) with the electrolytically-active species, comprising:
a) treating the aqueous or non-aqueous solution with at least one electrolytically-active product (for instance, but not limited to, combining at least a first reactant and a second reactant to produce an electrolytically-active reaction product which is formed in situ or before introduction in an aqueous or non-aqueous solution to provide a treated aqueous or non-aqueous solution);
b) introducing a sample of the treated aqueous solution in a selected amount into a measurement cell, wherein the measurement cell comprises a working electrode and an auxiliary electrode;
c) applying a constant current to the measurement cell while the working electrode and auxiliary electrode are in contact with the sample with monitoring of voltage difference across the working electrode and auxiliary electrode until detecting of a change in the voltage difference at a measured duration of time of applying the constant current;
d) generating a feedback signal using the measured duration of time of step c), wherein the measured duration of time is directly proportional to amount of the electrolytically-active product in the sample; and
e) optionally, using the feedback signal of step d) to control a rate of feeding of the electrolytically-active product or a component thereof, or a precursor thereof (such as, but not limited to, the first reactant and/or the second reactant) in step a).

19. The method of any preceding or following embodiment/feature/aspect, wherein the aqueous solution that is treated is industrial process water, waste water, cooling water, boiler water, municipal water, food processing water, or pulp.

20. The present invention also relates to an apparatus for measuring and controlling the concentration of an electrolytically-active species in an aqueous solution, comprising:
a) a measurement cell comprising a working electrode, an auxiliary electrode, and structure defining a cell volume for receiving a sample comprising an electrolytically-active species in an aqueous or non-aqueous solution;
b) a measurement circuit connected to the working electrode and the auxiliary electrode, wherein the measuring circuit is operable to i) provide a constant current to the measurement cell, ii) monitor and detect a change in voltage difference across the working electrode and auxiliary electrode, and iii) generate a feedback signal based on a measured parameter of the change in the voltage difference, wherein the measured parameter of the change in the voltage difference is directly proportional to the amount of the electrolytically-active species in the sample.

21. The apparatus of any preceding or following embodiment/feature/aspect, wherein the digital processing unit comprises a clock operable for measuring the parameter as a duration of time of applying the constant current until a change in the voltage difference is detected.

22. The apparatus of any preceding or following embodiment/feature/aspect, wherein the working electrode and the auxiliary electrode independently comprise graphite, glassy carbon, or any combinations thereof.

23. The apparatus and/or method of any preceding or following embodiment/feature/aspect, wherein instead of an aqueous solution, a non-aqueous solution is present and/or used.

The present invention can include any combination of these various features or embodiments above and/or below as set forth in sentences and/or paragraphs. Any combination of disclosed features herein is considered part of the present invention and no limitation is intended with respect to combinable features.

For purposes of the present invention, it is to be understood that every aspect of the present invention can apply to non-aqueous solutions that have conductivity for purposes of being detected in the methods and apparatus of the present invention.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:
1. A method for measuring and controlling the concentration of an electrolytically-active species in an aqueous or non-aqueous solution, comprising:
a) reacting at least one reactant that comprises a first reactant and a second reactant to produce a reaction mixture, wherein the reaction mixture comprises an electrolytically-active species in aqueous solution;
b) introducing a sample of the reaction mixture comprising the electrolytically-active species into a measurement cell, wherein the measurement cell comprises a working electrode and an auxiliary electrode;

c) applying a constant current to the measurement cell while the working electrode and auxiliary electrode are in contact with the sample with monitoring of voltage difference across the working electrode and auxiliary electrode until a change in the voltage difference is detected;

d) generating a feedback signal based on a measured parameter of the change in the voltage difference, wherein the measured parameter of the change in the voltage difference is a measured duration of time of applying the constant current in step c) until the voltage difference is detected, and wherein the measured duration of time is directly proportional to the amount of the electrolytically-active species in the sample; and e) using the feedback signal of step d) to control the amount of the electrolytically-active species, or a precursor thereof, or a component thereof, or a reactant for producing the electrolytically-active species in the aqueous solution or non-aqueous solution, wherein the first reactant is an alkali metal hypochlorite, the second reactant is ammonia, and the electrolytically-active species is monochloramine, and wherein the measured parameter of the change in the voltage difference is a measured time interval beginning when the constant current is applied to the measurement cell and ending when the applied voltage has reached a level at which all of the monochloramine has been depleted and the voltage difference is detected.

2. The method of claim 1, wherein said using the feedback signal in e) comprises using the feedback signal to control a rate of feeding of the at least one reactant to a process unit wherein the reacting occurs.

3. The method claim 1, wherein the measurement cell has only the working electrode and the auxiliary electrode as electrodes of the measurement cell.

4. The method of claim 1, wherein the constant current is in the range of from about 10 milliampere (mA) to about 1 ampere (A).

5. The method of claim 1, wherein the working electrode and the auxiliary electrode independently comprise graphite, glassy carbon, or any combinations thereof.

6. The method of claim 1, wherein the selected amount of the sample is from about 1 mL to about 10 mL, wherein the measurement cell has a fixed cell volume which defines the selected amount of sample.

7. The method of claim 1, wherein the reacting of the at least one reactant comprises combining the first reactant and the second reactant to form the electrolytically-active species in situ in the aqueous solution; wherein the feedback signal is used to control a rate of feeding of at least one of the first reactant and the second reactant.

8. A method for measuring and/or controlling the concentration of an electrolytically-active species in an aqueous or non-aqueous solution treated with the electrolytically-active species, comprising:

a) adding at least one electrolytically-active product comprising monochloramine to an aqueous solution to provide a treated aqueous or non-aqueous solution;

b) introducing a sample of the treated aqueous solution or treated non-aqueous solution into a measurement cell, wherein the measurement cell comprises a working electrode and an auxiliary electrode;

c) applying a constant current to the measurement cell while the working electrode and auxiliary electrode are in contact with the sample for electrolytic reduction of the monochloramine to chloride ion and ammonia with monitoring of voltage difference across the working electrode and auxiliary electrode until detecting of a change in the voltage difference at a measured duration of time of applying the constant current;

d) generating a feedback signal using the measured duration of time of step c), wherein the measured duration of time is directly proportional to amount of the electrolytically-active product in the sample; and e) using the feedback signal of step d) to control the amount of the electrolytically-active product, or a precursor thereof, or a component thereof in the aqueous solution or non-aqueous solution.

9. The method of claim 8, wherein the aqueous solution that is treated is industrial process water, waste water, cooling water, boiler water, municipal water, food processing water, or pulp.

* * * * *